(12) United States Patent
Arnar et al.

(10) Patent No.: US 12,350,444 B2
(45) Date of Patent: Jul. 8, 2025

(54) LOCKING GUIDE CATHETER HUBS (71) Applicant: St. Jude Medical, Cardiology Division, Inc., St. Paul, MN (US)

(72) Inventors: Bernhard Arnar, Minnetrista, MN (US); Nicholas V. Jepson, Buffalo, MN (US); Jeremiah Blue, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1373 days.

(21) Appl. No.: 16/233,282

(22) Filed: Dec. 27, 2018

(65) Prior Publication Data

US 2019/0224450 A1 Jul. 25, 2019

Related U.S. Application Data

(60) Provisional application No. 62/619,431, filed on Jan. 19, 2018.

(51) Int. Cl.
*A61M 25/00* (2006.01)
*A61M 25/06* (2006.01)
(Continued)

(52) U.S. Cl.
CPC .... *A61M 25/0097* (2013.01); *A61M 25/0662* (2013.01); *A61M 25/09041* (2013.01);
(Continued)

(58) Field of Classification Search
CPC .... A61M 2025/09125; A61M 25/0097; A61M 39/06; A61M 39/0613; A61M 2039/0673;
(Continued)

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| DE | 102005003632 A1 | 8/2006 |
| EP | 1129744 A1 | 9/2001 |

(Continued)

OTHER PUBLICATIONS

Ruiz, Carlos, Overview of PRE-CE Mark Transcatheter Aortic Valve Technologies, Euro PCR dated May 25, 2010.
(Continued)

*Primary Examiner* — Michael J Tsai
*Assistant Examiner* — Neeraja Gollamudi
(74) *Attorney, Agent, or Firm* — SLEMAN & LUND LLP (57) ABSTRACT

A delivery device for an implantable medical device may include an inner shaft configured to retain the implantable medical device at its distal end, an outer shaft slidably disposed about the inner shaft, and a locking hub affixed to the outer shaft. The locking hub may include a housing, a piston element in the housing, an actuator operatively coupled to the piston element, and a clamping gasket made of a compressible material and disposed in the housing. The actuator may be movable relative to the housing between unlocked and locked conditions. The clamping gasket may have a lumen defining a first diameter with the actuator in the unlocked condition and a second diameter with the actuator in the locked condition, the second diameter being less than the first diameter. The outer shaft and the locking hub may be fixed to the inner shaft with the actuator in the locked condition.

13 Claims, 3 Drawing Sheets

(51) Int. Cl.
  *A61M 25/09* (2006.01)
  *A61M 39/06* (2006.01)
  *A61N 1/372* (2006.01)

(52) U.S. Cl.
  CPC ..... *A61M 25/0905* (2013.01); *A61N 1/37205* (2013.01); *A61M 2025/0681* (2013.01); *A61M 39/06* (2013.01)

(58) Field of Classification Search
  CPC .......... A61M 2025/0079; A61M 39/00; A61M 39/10; A61M 39/1011; A61M 2039/1016; A61M 2039/1027; A61M 39/1055; A61M 2039/1061; A61M 2039/1077; A61M 2039/1083; A61M 2039/1088
  See application file for complete search history.

(56) References Cited

U.S. PATENT DOCUMENTS

| | | | |
|---|---|---|---|
| 4,723,550 A * | 2/1988 | Bales | A61M 39/0613 606/191 |
| 5,062,648 A * | 11/1991 | Gomringer | A61B 17/320758 277/560 |
| 5,078,720 A | 1/1992 | Burton et al. | |
| 5,415,664 A | 5/1995 | Pinchuk | |
| 5,484,444 A | 1/1996 | Braunschweiler et al. | |
| 5,591,137 A * | 1/1997 | Stevens | A61M 39/0613 604/296 |
| 5,702,418 A | 12/1997 | Ravenscroft | |
| 5,824,041 A | 10/1998 | Lenker et al. | |
| 5,843,167 A | 12/1998 | Dwyer et al. | |
| 5,924,424 A | 7/1999 | Stevens et al. | |
| 5,968,068 A | 10/1999 | Dehdashtian et al. | |
| 5,980,533 A | 11/1999 | Holman | |
| 6,077,297 A | 6/2000 | Robinson et al. | |
| 6,269,819 B1 | 8/2001 | Oz et al. | |
| 6,306,141 B1 | 10/2001 | Jervis | |
| 6,391,050 B1 | 5/2002 | Broome | |
| 6,468,299 B2 | 10/2002 | Stack et al. | |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 8,840,663 B2 | 9/2014 | Salahieh et al. | |
| 2003/0050694 A1 | 3/2003 | Yang et al. | |
| 2004/0210304 A1 | 10/2004 | Seguin et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 * | 5/2007 | Dehdashtian | A61F 2/2433 623/2.11 |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0233007 A1 * | 10/2007 | Adams | A61M 25/0097 604/168.01 |
| 2007/0239271 A1 | 10/2007 | Nguyen | |
| 2007/0244552 A1 | 10/2007 | Salahieh et al. | |
| 2008/0071369 A1 | 3/2008 | Tuval et al. | |
| 2008/0147182 A1 | 6/2008 | Righini et al. | |
| 2009/0054975 A1 | 2/2009 | del Nido et al. | |
| 2009/0259200 A1 * | 10/2009 | Lampropoulos | A61M 39/0613 604/249 |
| 2010/0004740 A1 | 1/2010 | Seguin et al. | |
| 2010/0036329 A1 * | 2/2010 | Razack | A61M 39/0613 604/256 |
| 2010/0286768 A1 | 11/2010 | Alkhatib | |
| 2010/0298931 A1 | 11/2010 | Quadri et al. | |
| 2011/0224678 A1 | 9/2011 | Gabbay | |
| 2018/0104449 A1 * | 4/2018 | Arnar | A61N 1/3756 |

FOREIGN PATENT DOCUMENTS

| | | |
|---|---|---|
| EP | 1157673 A2 | 11/2001 |
| EP | 1 926 455 A2 | 6/2008 |
| WO | 02067782 A2 | 9/2002 |
| WO | 07071436 A2 | 6/2007 |
| WO | 08070797 A2 | 6/2008 |
| WO | 10051025 A1 | 5/2010 |
| WO | 10087975 A1 | 8/2010 |

OTHER PUBLICATIONS

"Percutaneous Aortic Valve Replacement: Resection Before Implantation", Quaden, Rene et al., European J. of Cardio-Thoracic Surgery, vol. 27, No. 5, May 2005, pp. 836-840.

* cited by examiner

LOCKING GUIDE CATHETER HUBS

CROSS-REFERENCE TO RELATED APPLICATION

The present application claims the benefit of the filing date of U.S. Provisional Patent Application No. 62/619,431, filed Jan. 19, 2018, the disclosure of which is hereby incorporated herein by reference.

BACKGROUND OF THE INVENTION

The present invention is related to implantable medical devices and, more particularly, to systems and methods for implanting a medical device.

Numerous medical devices exist today, including but not limited to implantable pacemakers, implantable cardioverter-defibrillators ("ICDs"), and the like. Medical devices of this type that are implantable (hereinafter, generally "implantable medical devices" or "IMDs") are configured to be implanted within the patient anatomy and commonly employ one or more leads with electrodes that either receive or deliver voltage, current or other electromagnetic pulses (generally "energy") from or to an organ and/or tissue for diagnostic and/or therapeutic purposes.

Typically, an intra-cardiac IMD is introduced into the heart through a catheter-based delivery device. In general, the IMD may be connected to the delivery device in a docked state in which the IMD is securely attached to a catheter of the delivery device. In the docked state, the delivery device may be operated to guide the IMD to an implant site. Once the IMD is proximate to the implant site, the delivery device may be used to torque the IMD into patient tissue.

Once the IMD is secured into patient tissue, the IMD may be moved into a tethered state with respect to the delivery device. In the tethered state, the IMD is deployed from the delivery device, but remains connected thereto. In one known system and method, two separate and distinct tethers connect the IMD to the catheter of the delivery device in the tethered state. An implanting physician may test the IMD in the tethered state to make sure that the IMD is securely and electrically connected to patient tissue at a desired location. If the physical and/or electrical connection between the IMD and the patient tissue is less than optimal, the IMD may be re-docked to the catheter of the delivery device so that the IMD may be moved to a better implanted position.

Once the implanting physician is satisfied with the location of the IMD within the patient anatomy, the IMD is transitioned from the tethered state to a released state. In the released state, the IMD is disconnected from the catheter of the delivery device.

Despite the various improvements that have been made to IMD delivery systems, conventional systems suffer from some shortcomings. An IMD may rely on a helical, screw-in anchoring system that is used to affix the IMD to target tissue, such as the inside of the heart wall. During the implantation procedure, a sheath may at last partially surround the IMD and the helix. This sheath may protect the helix from damage while the IMD is navigated through the anatomy to the implant site and also may protect the vasculature from inadvertent puncture by the helix. An IMD delivery device may rely on the seal in a hemostasis hub to hold the sheath in the proper location during navigation of the IMD through the vasculature. Such a hemostasis seal may not grip the catheter tightly, so the sheath may slip backwards during manipulation of the catheter of the delivery device, thereby unintentionally exposing the helix.

There therefore is a need for further improvements to the devices, systems, and methods for transcatheter delivery of IMDs, and in particular, for transcatheter delivery of leadless pacemakers. Among other advantages, the present invention may address one or more of these needs.

BRIEF SUMMARY OF THE INVENTION

Described herein is a delivery device for an implantable medical device. The delivery device may include an inner shaft configured to retain the implantable medical device at its distal end, an outer shaft slidably and coaxially disposed about the inner shaft, and a locking hub affixed to the outer shaft. The locking hub may include a housing having an internal recess, a piston element disposed in the internal recess, an actuator operatively coupled to the piston element, and a clamping gasket made of a compressible material and disposed in the internal recess. The piston element may be translatable within the internal recess along a longitudinal axis of the locking hub. The actuator may have a portion thereof extending outside of the housing and accessible for grasping by a user. The actuator may be movable relative to the housing between an unlocked condition and a locked condition. The clamping gasket may have a lumen extending therethrough along the longitudinal axis. The lumen may have a first diameter with the actuator in the unlocked condition and a second diameter with the actuator in the locked condition, the second diameter being less than the first diameter. The outer shaft and the locking hub may be slidable along the inner shaft with the actuator in the unlocked condition. The outer shaft and the locking hub may be fixed to the inner shaft with the actuator in the locked condition.

Also described herein is a method of delivering an implantable medical device to a target location, the method including providing a delivery device having an inner shaft configured to releasably retain the implantable medical device at a distal end of the delivery device, an outer shaft slidably and coaxially disposed about the inner shaft, the outer shaft affixed to a sheath that is configured to selectively cover the implantable medical device, and a locking hub having a housing affixed to the outer shaft and an actuator movable relative to the housing between an unlocked condition and locked condition, the locking hub having a hemostasis gasket slidably disposed around the inner shaft.

The method may also include placing the actuator in the locked condition, so that the outer shaft and the locking hub are releasably fixed to the inner shaft, and inserting the distal end of the delivery device into vasculature of a patient. The method may also include advancing the distal end of the delivery device to the target location, moving the actuator to the unlocked condition, so that the outer shaft and the locking hub are slidable along the inner shaft, and sliding the sheath relative to the inner shaft to uncover the implantable medical device. The method may also include releasing the implantable medical device from the inner shaft and removing the distal end of the delivery device from the vasculature of the patient. The hemostasis gasket may provide a liquid-tight seal against the inner shaft, the liquid-tight seal being maintained when the actuator is in the unlocked condition and when the actuator is in the locked condition.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. As used herein, the terms "generally," "substantially," "approximately," and "about" are intended to mean that slight deviations from absolute are included within the scope of the term so modified.

Figure 1A:
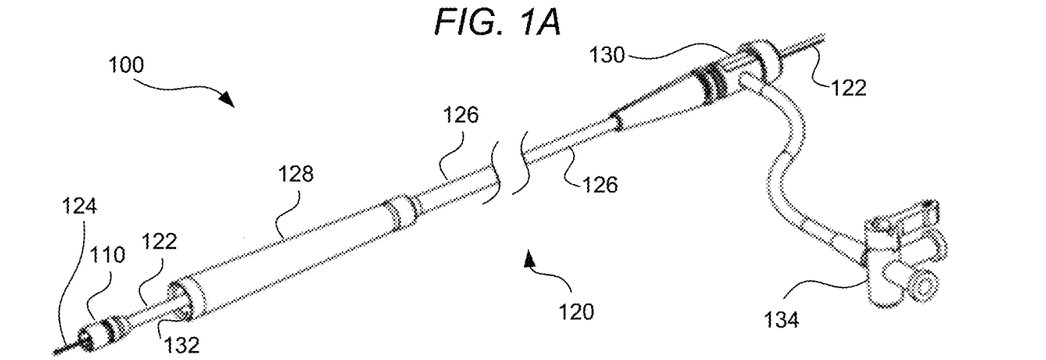
FIG. 1A is a perspective view of the catheter assembly of a delivery device for delivering an implantable medical device (IMD) into a patient, a sheath of the medical device being withdrawn to expose the IMD.
Figure 1B:
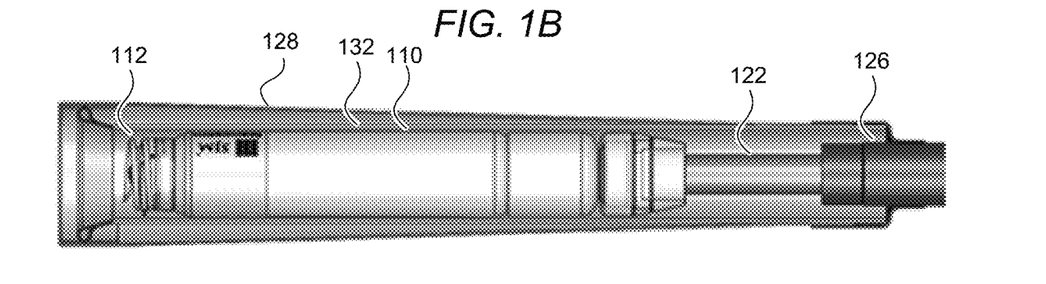
FIG. 1B is a side view of a distal portion of the delivery device and the IMD of FIG. 1A, shown with a longitudinal cross-section of the sheath covering the IMD.

Referring now to FIGS. 1A and 1B to illustrate the structure and function of the present invention, an exemplary transfemoral delivery device 100 for delivering an IMD 110 having a helix 112 into a patient has a catheter assembly 120 for delivering the IMD to and deploying the IMD at a target location. The helix 112 may be a helical, screw-in anchor that may be used to affix the IMD 110 to target tissue, such as the inside of the heart wall. The delivery device 100 may also include an operating handle (not shown) for controlling deployment of the IMD 110 from the catheter assembly 120.

The catheter assembly 120 may include an inner shaft 122 that is configured to removably retain the IMD 110 at its distal end. The inner shaft 122 may extend from its distal end to a proximal end at the operating handle. The catheter assembly 120 may also include a guide wire 124 that may extend through a lumen of the inner shaft 122 and an outer shaft 126 that is slidably and coaxially arranged over the inner shaft.

The outer shaft 126 is affixed to a sheath 128 at its distal end and is affixed to a hemostasis valve 130 at its proximal end. The outer shaft 126, sheath 128, and hemostasis valve 130 can be retracted together along the inner shaft 122 to expose the IMD 110 or advanced together along the inner shaft to cover the IMD. The sheath 128 has a compartment 132 therein configured to receive the IMD 110 when the sheath is advanced distally with respect to the inner shaft 122.

The hemostasis valve 130 includes an internal gasket adapted to create a seal between the inner shaft 122 and the proximal end of the outer shaft 126. The hemostasis valve 130 is in fluid communication with the compartment 132 via a space between the inner shaft 122 and the outer shaft 126. The compartment 132 is configured to be flushed by admitting a flushing liquid into the hemostasis valve 130 through a flush port assembly 134. Although saline is typically used as the flush liquid, any other appropriate liquid may be used. It is desirable to flush the compartment 132 in order to de-air (i.e., remove air pockets or air bubbles) the area in and around the IMD 110. Additional features of the delivery device 100 may be found in U.S. Pat. No. 8,615,310 and U.S. Patent Publication No. 2016/0067447, the disclosures of which are both hereby incorporated by reference herein.

FIGS. 2A-2D show a locking hub 230 that is suitable for use with the delivery device 100 of FIGS. 1A and 1B in place of the hemostasis valve 130. The locking hub has a housing 240 having a lumen including a proximal recess 241 contiguous with a distal socket 242 configured to fixedly receive the proximal end of the outer shaft 126, and configured to slidably receive a portion of the inner shaft 122 extending therethrough within the outer shaft. The housing 240 is configured to receive the inner shaft 122 extending along a longitudinal axis L1 therein through the proximal recess 241 and the distal socket 242. The housing 240 has a flushing port 243 that is in fluid communication with the flush port assembly 134. A slot 244 formed at the proximal end of the housing 240 terminates at a proximal-facing surface 245, and two coaxially aligned apertures 246 extend through the housing 240 at the recess 241 to define a pivot axis L2 transverse to the longitudinal axis L1.

The locking hub 230 may contain a lever cam 250 comprising a pair of side members 251 positioned on opposite sides of the inner shaft 122. The side members 251 are joined to one another at a grasping portion 252 extending out of the recess 241, and at a linking member 253 having a contact portion 254 configured to abut the inner shaft 122 when the lever cam is in the locked position shown in FIG. 2B. The lever cam 250 has a pair of bosses 255 projecting laterally from the respective side members 251. The bosses 255 are journaled in the apertures 246 to enable the lever cam 250 to be rotated about the pivot axis L2 between the unlocked position shown in FIG. 2A and the locked position in FIG. 2B. As will be explained more fully below, when the lever cam 250 is in the locked position, the relative longitudinal locations of the inner shaft 122 and the outer shaft 126 are fixed to one another. When the lever cam 250 is in the unlocked position, the outer shaft 126 and the locking hub 230 are translatable together along the inner shaft 122 in directions of the longitudinal axis L1.

Figures 2A, 2C:
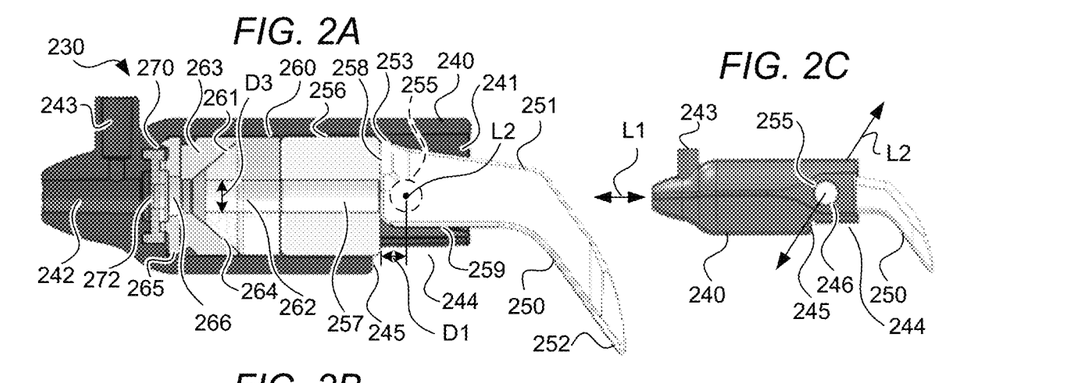
FIG. 2A is a longitudinal cross-section through a locking hub suitable for use with the delivery device of FIGS. 1A and 1B, shown in an unlocked position.
FIG. 2C is a side view of the locking hub of FIG. 2A.
Figure 2B:
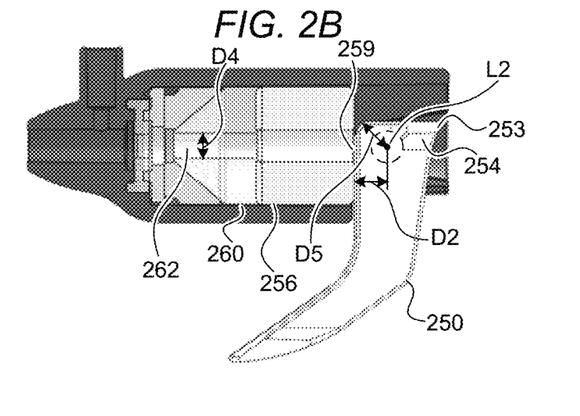
FIG. 2B is a longitudinal cross-section through the locking hub of FIG. 2A, shown in a locked position.
Figure 2D:
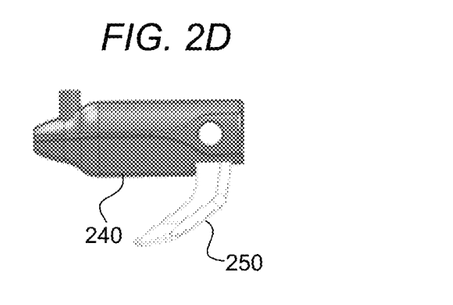
FIG. 2D is a side view of the locking hub of FIG. 2B.

The lever cam 250 may abut a piston 256 having a lumen 257 extending along the longitudinal axis L1, which may in turn abut a clamping gasket 260 having a conical distal surface 261 and a lumen 262 also extending along the longitudinal axis. The conical distal surface 261 of the clamping gasket 262 may be partially received within a first washer 263 having a conical recess 264 configured to mate with the conical distal surface of the clamping gasket. The first washer 263 may abut a second washer 265 having an opening 266 extending therethrough along the longitudinal axis L1. The first and second washers 263 and 265 may be formed as separate components or as a single unitary component having a single continuous opening extending therethrough. The second washer 265 may abut a hemostasis gasket 270 having an opening 272 extending therethrough along the longitudinal axis L1.

The socket 242, the lumens 257 and 262, and the openings 266 and 272 are all axially aligned along the longitudinal axis L1, such that the inner shaft 122 can extend therethrough. Regardless of whether the lever cam 250 is in the locked position or the unlocked position, the hemostasis gasket 270 is configured to create a liquid-tight seal around the inner shaft 122, thereby preventing blood from leaking out of the proximal end of the catheter assembly 120. However, the force applied by the hemostasis gasket 270 against the inner shaft 122 is low enough to permit the locking hub 230 and the outer shaft 126 to slide longitudinally along the inner shaft when the user retracts the outer shaft and the sheath 128 to deploy the IMD 110.

The lever cam 250 is configured to compress the clamping gasket 260 along the longitudinal axis L1 when moved from the unlocked position shown in FIG. 2A to the locked position shown in FIG. 2B. The pivot axis L2 about which the lever cam 250 rotates is located a first distance D1 from a first abutment surface 258 of the lever cam and a second distance D2 from a second abutment surface 259 of the lever cam, the first distance being less than the second distance. When the lever cam 250 is in the unlocked position shown in FIG. 2A, the first abutment surface 258 abuts the proximal end of the piston 256, and when the lever cam is in the locked position shown in FIG. 2B, the second abutment surface 259 abuts the proximal end of the piston. Since the second distance D2 is greater than the first distance D1, when the lever cam 250 is moved from the unlocked position to the locked position, the piston 256 is translated distally along the longitudinal axis L1 by a distance equal to the difference between the first distance D1 and the second distance D2.

When the piston 256 is translated distally along the longitudinal axis L1, the clamping gasket 260 is compressed along the longitudinal axis. The clamping gasket 260 is made of a compressible material, such as silicone, rubber, or another polymer. When the clamping gasket 260 is compressed along the longitudinal axis, the conical distal surface 261 of the clamping gasket slides distally along the conical recess 264 of the first washer 263, and the lumen 262 of the clamping gasket radially compresses from a first diameter D3 (FIG. 2A) to a second diameter D4 (FIG. 2B), the second diameter being less than the first diameter. This reduction in diameter of the lumen 262 of the clamping gasket 260 causes the clamping gasket to compress around the outer surface of the inner shaft 122, thereby fixing the longitudinal position of the inner shaft relative to the outer shaft 126. As a result, the longitudinal position of the IMD 110 relative to the sheath 128 is also fixed so that the IMD is not unintentionally unsheathed as the delivery device 100 is advanced through the vasculature of a patient. When the lever cam 250 is moved from the locked position to the unlocked position, the piston 256 is able to translate proximally along the longitudinal axis L1, relieving the pressure on the clamping gasket 260 so that the lumen 262 of the clamping gasket radially expands from the second diameter D4 back to the first diameter D3. This radial expansion releases the inner shaft 122 so that the locking hub 230 and the outer shaft 126 may again slide longitudinally along the inner shaft, thereby enabling the sheath 128 to be retracted from around the IMD 110.

The lever cam 250 is configured such that both the unlocked position and the locked position are mechanically stable. For example, when the lever cam 250 is in the unlocked position shown in FIG. 2A, the compression of the clamping gasket 260 is at a minimum. That is, the distance between the proximal end of the piston 256 and the pivot axis L2 of the lever cam 250 is the first distance D1, which is the smallest such distance permitted in any position of the lever cam. Therefore, any motion of the lever cam 250 in either rotational direction will begin to compress the clamping gasket 260 or will further compress the clamping gasket, so the clamping gasket will exert a force against the first abutment surface 258 of the lever cam that will tend to resist any rotation of the lever cam, thereby preventing the lever cam from easily rotating as a result of unintentional contact by a user.

When the lever cam 250 is in the locked position shown in FIG. 2B, the compression of the clamping gasket 260 is at a local minimum. That is, the distance between the proximal end of the piston 256 and the pivot axis L2 of the lever cam 250 is the second distance D2, but any movement of the lever cam 250 back towards the unlocked position will further compress the clamping gasket, so the clamping gasket will exert a force against the second abutment surface 259 of the lever cam that will tend to resist rotation of the lever cam back towards the unlocked position, thereby preventing the lever cam from easily rotating as a result of unintentional contact by a user. If a user desires to move the lever cam 250 from the locked position to the unlocked position, the user must apply sufficient compressive force to the clamping gasket 260 to distally translate the piston 256 a third distance D5, which is greater than the second distance D2. When the lever cam 250 is in the locked position, physical interference between the proximal-facing surface 245 at the end of the slot 244 and the lever cam and physical interference between the contact portion 254 of the linking member 253 and the inner shaft 122 prevents the lever cam from rotating beyond the locked position.

FIGS. 3A-3D show a locking hub 330 that is a variant of the locking hub 230 and also suitable for use with the delivery device 100 of FIGS. 1A and 1B in place of the hemostasis valve 130. The locking hub 330 has a housing 340 having a lumen including a proximal recess 341 contiguous with a distal socket 342 configured to fixedly receive the proximal end of the outer shaft 126, and configured to slidably receive a portion of the inner shaft 122 extending within the outer shaft. The inner shaft 122 extends from the distal socket 342 through the proximal recess 341 along a longitudinal axis L1. The housing 340 has a flushing port 343 that is in fluid communication with the flush port assembly 134. The locking hub 330 may have a pair of wings 344 extending outwardly from the housing 340 along an axis L2 transverse to the longitudinal axis. The wings 344 may be configured to be grasped by a user of the locking hub 330.

The locking hub 330 may have a circumferential flange 345 projecting radially outwardly from the housing 340 and extending in a circumferential direction about the longitudinal axis L1. Two protrusions 347 and 348 may be provided at predefined circumferential locations separated by a predetermined angular distance along the flange 345. As shown in FIGS. 3A-3D, the protrusions 347 and 348 are separated by approximately 90°, but may be separated by other angular distances, such as 30°, 45°, 60°, 120°, 180°, 270°, or other angles in between, among others. The housing 340 may have external threads 349 at its proximal end.

Figure 3A:
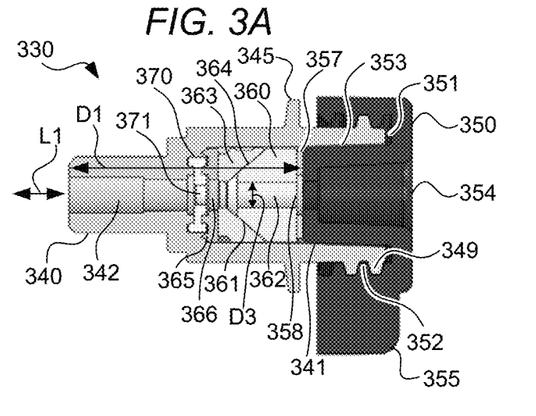
FIG. 3A is a longitudinal cross-section through a locking hub suitable for use with the delivery device of FIGS. 1A and 1B, according to another embodiment, shown in an unlocked position.
Figure 3B:
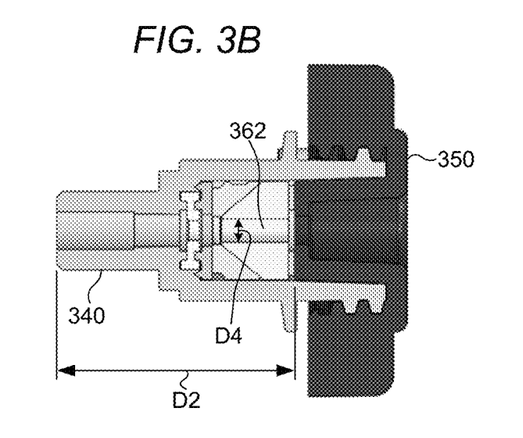
FIG. 3B is a longitudinal cross-section through the locking hub of FIG. 3A, shown in a locked position.
Figure 3C:
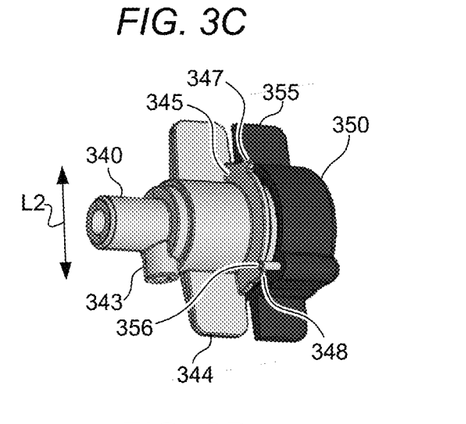
FIG. 3C is a perspective view of the locking hub of FIG. 3A.
Figure 3D:
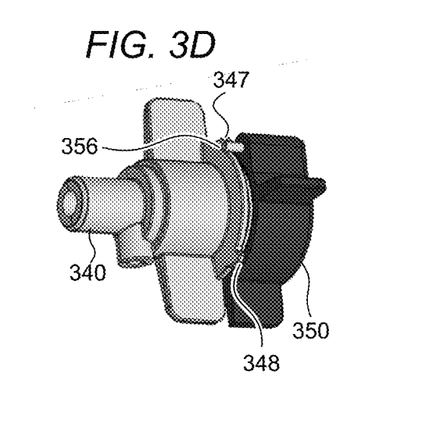
FIG. 3D is a perspective view of the locking hub of FIG. 3B.

The locking hub 330 may contain a cap or actuator 350 that is configured to be rotated about the longitudinal axis L1 between the unlocked position shown in FIG. 3A and the locked position shown in FIG. 3B. When the cap 350 is in the locked position, the relative longitudinal locations of the inner shaft 122 and the outer shaft 126 are fixed to one another, as will be explained more fully below. When the lever cam 350 is in the unlocked position, the outer shaft 126 and the locking hub 330 are translatable together along the inner shaft 122 in directions of the longitudinal axis L1.

The cap 350 may define an annular recess 351 extending inwardly from a distal end of the cap and extending circumferentially about the longitudinal axis L1. An outer wall of the annular recess 351 may have internal threads 352 configured to mate with the external threads 349 of the housing 340, such that the cap 350 may be rotatably coupled to the housing 340.

The cap 350 may have a piston portion 353 defined by an inner wall of the annular recess 351 and configured to be received within the proximal recess 341 of the housing 340. The cap 350 may define a lumen 354 extending through the piston portion 353 along the longitudinal axis L1. Three wings 355 may extend outwardly from the cap 350 in respective lateral directions transverse to the longitudinal axis L1. The wings 355 may be configured to be grasped by a user of the locking hub 330 so that the user can rotate the cap 350 relative to the housing 340.

The cap 350 may have a pin 356 extending from the distal edge of the cap in a direction parallel to the longitudinal axis L1. The pin 356 may be configured to slide along the circumferential flange 345 between the protrusions 347 and 348 as the cap 350 is rotated about the longitudinal axis L1. The protrusions 347 and 348 may act as movement restrictors to limit the circumferential movement of the pin 356 relative to the housing 340, thereby together defining a range of rotation of the cap 350 about equal to the extent of the angular separation of the protrusions, e.g., approximately 90°, that is, about one-quarter turn. In other words, when the cap 350 is rotated relative to the housing 340, one surface of the pin 356 may abut a surface of the protrusion 347 to limit the rotation of the cap 350 in one direction, and another surface of the pin 356 may abut a surface of the protrusion 348 to limit the rotation of the cap 350 in the opposite direction.

The piston portion 353 of the cap 350 may abut a first washer 357 having an opening 358 extending therethrough along the longitudinal axis L1. In some embodiments, the first washer 357 may be omitted. The first washer 357 may in turn abut a clamping gasket 360 having a conical distal surface 361 and a lumen 362 extending therethrough along the longitudinal axis. The conical distal surface 361 of the clamping gasket 360 may be partially received within a second washer 363 having a conical recess 364 configured to mate with the conical distal surface of the clamping gasket. The second washer 363 may abut a third washer 365 having an opening 366 extending therethrough along the longitudinal axis L1. The second and third washers 363 and 365 may be formed as separate components or as a single unitary component having a single continuous opening extending therethrough. The third washer 365 may abut a hemostasis gasket 370 having an opening 371 extending therethrough along the longitudinal axis L1.

The socket 342, the lumens 354 and 362, and the openings 358, 366, and 371 are all axially aligned along the longitudinal axis L1, such that the inner shaft 122 can extend therethrough. Regardless of whether the cap 350 is in the locked position or the unlocked position, the hemostasis gasket 370 is configured to create a liquid-tight seal around the inner shaft 122, thereby preventing blood from leaking out of the proximal end of the catheter assembly 120. However, the force applied by the hemostasis gasket 370 against the inner shaft 122 is low enough to permit the locking hub 330 and the outer shaft 126 to slide longitudinally along the inner shaft when the user retracts the outer shaft and the sheath 128 to deploy the IMD 110.

The cap 350 is configured to compress the clamping gasket 360 along the longitudinal axis L1 when moved from the unlocked position shown in FIG. 3A to the locked position shown in FIG. 3B. When the cap 350 is in the unlocked position shown in FIG. 3A, the distal end of the piston portion 353 of the cap is located a first distance D1 from the distal end of the housing 340, and when the cap is in the locked position shown in FIG. 3B, the distal end of the piston portion is located a second distance D2 from the distal end of the housing, the second distance being less than the first distance. Accordingly, when the cap 350 is moved from the unlocked position shown in FIG. 3A to the locked position in FIG. 3B, the cap is translated distally along the longitudinal axis L1 by a distance equal to the difference between the first distance D1 and the second distance D2.

When the cap 350 is translated distally along the longitudinal axis L1, the clamping gasket 360 is compressed along the longitudinal axis. The clamping gasket 360 is made of a compressible material, such as silicone, rubber, or another polymer. When the clamping gasket 360 is compressed along the longitudinal axis, the conical distal surface 361 of the clamping gasket slides distally along the conical recess 364 of the second washer 363, and the lumen 362 of the clamping gasket radially compresses from a first diameter D3 (FIG. 3A) to a second diameter D4 (FIG. 3B), the second diameter being less than the first diameter. This reduction in diameter of the lumen 362 of the clamping gasket 360 causes the clamping gasket to compress around the outer surface of the inner shaft 122, thereby fixing the longitudinal position of the inner shaft relative to the outer shaft 126. As a result, the longitudinal position of the IMD 110 relative to the sheath 128 is also fixed so that the IMD is not unintentionally unsheathed as the delivery device 100 is advanced through the vasculature of a patient. When the cap 350 is moved from the locked position to the unlocked position, the piston portion 353 of the cap moves proximally along the longitudinal axis L1, relieving the pressure on the clamping gasket 360 so that the lumen 362 of the clamping gasket radially expands from the second diameter D4 back to the first diameter D3. This radial expansion releases the inner shaft 122 so that the locking hub 330 and the outer shaft 126 may again slide longitudinally along the inner shaft, enabling the sheath 128 to be retracted from around the IMD 110.

The locking hub 330 is configured such that the unlocked position, the locked position, and all intermediate positions therebetween are mechanically stable. For example, when the cap 350 is in the unlocked position shown in FIG. 3A, the compression of the clamping gasket 360 is at a minimum. That is, the distance between the distal end of the piston portion 353 and the distal end of the housing 340 is the first distance D1, which is the farthest distance permitted in any position of the cap 350. Therefore, any rotational motion of the cap 350 will begin to compress the clamping gasket 360 or will further compress the clamping gasket, so the clamping gasket will exert a force against the distal end of the piston portion 353 and the cap that will increase the friction between the threads 349 and 352, thereby resisting rotation of the cap and preventing the cap from easily rotating as a result of unintentional contact by a user.

When the cap 350 is in the locked position shown in FIG. 3B or in any intermediate position between the locked and unlocked positions, the distance between the distal end of the piston portion 353 and the distal end of the housing 340 is less than the first distance D1, so the clamping gasket 360 will provide a force against the distal end of the piston portion 353 greater than the force provided when the cap is in the unlocked position. This force against the distal end of the piston portion results in friction between the threads 349 and 352, thereby resisting rotation of the cap and preventing the cap from easily rotating as a result of unintentional contact by a user. In any position of the cap 350, when a user desires to move the cap from the locked position to the unlocked position or vice versa, the user must apply sufficient rotating force to the cap to overcome the friction between the threads 349 and 352.

Figure 3E:
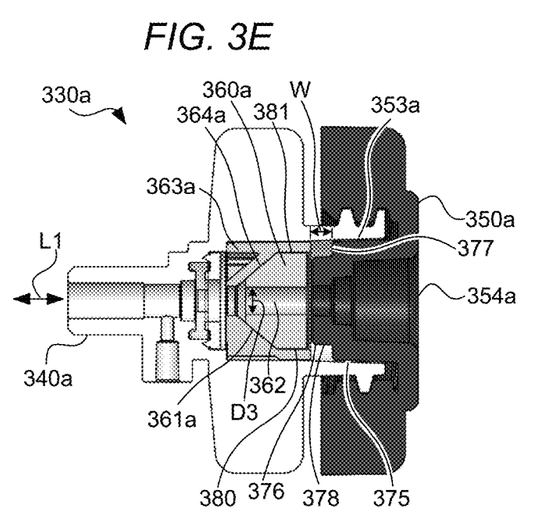
FIG. 3E is a longitudinal cross-section through a locking hub that is a variation of the locking hub of FIG. 3A, shown in an unlocked position.
Figure 3F:
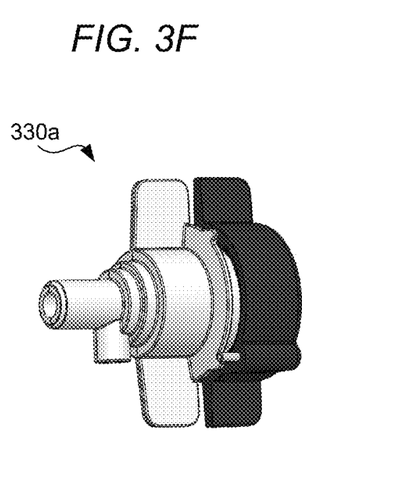
FIG. 3F is a perspective view of the locking hub of FIG. 3E.

FIGS. 3E-3F show a locking hub 330a that is a variant of the locking hub 330 and also suitable for use with the delivery device 100 of FIGS. 1A and 1B in place of the hemostasis valve 130. The locking hub 330a has a housing 340a generally similar in structure and function to the housing 340. The locking hub 330a may contain a cap 350a that is configured to be rotated about the longitudinal axis L1 between the unlocked position shown in FIG. 3E and a locked position (not shown). The cap 350a may have a piston portion 353a configured to be received within the housing 340a. The piston portion 353a may have a wide portion 375 and a narrow portion 376, with a step surface 377 defined between the outer surfaces of the wide portion and the narrow portion. The narrow portion 376 may define a cylindrical outer surface 378. The cylindrical outer surface 378 may define a width W in a direction parallel to the longitudinal axis L1.

The piston portion 353a of the cap 350a may abut a clamping gasket 360a having a conical distal surface 361a and a lumen 362 extending therethrough along the longitudinal axis. The conical distal surface 361a of the clamping gasket 360a may be fully received within a second washer 363a having a conical recess 364a configured to mate with the conical distal surface of the clamping gasket. (In this embodiment, the first washer 357 has been omitted.) The clamping gasket 360a may have a cylindrical lateral surface 380 proximal to the conical distal surface 361a that may be fully received within the second washer 363a. A cylindrical recess 381 of the second washer 363a proximal to the conical recess 364a may be configured to mate with the cylindrical lateral surface 380 of the glamping gasket 360a. The cap 350a is configured to compress the clamping gasket 360a along the longitudinal axis L1 when moved from the unlocked position to the locked position. When the cap 350 is moved from the unlocked position shown in FIG. 3E to the locked position, the cap is translated distally along the longitudinal axis L1 by a distance less than or equal to the width W of the cylindrical outer surface 378 of the narrow portion 376 of the piston portion 353a, depending on the particular design chosen.

When the cap 350 is in the unlocked position shown in FIG. 3E, the narrow portion 376 of the piston portion 353a does not extend into the cylindrical recess 381 of the second washer 363a, and the step surface 377 is spaced apart from the proximal end of the second washer by a distance equal to the width W of the cylindrical outer surface 378 of the narrow portion. In one example, when the cap 350a is in the locked position, the narrow portion 376 of the piston portion 353a may partially extend into the cylindrical recess 381 of the second washer 363a, and the step surface 377 may be spaced apart from the proximal end of the second washer by a distance less than the width W of the cylindrical outer surface 378 of the narrow portion. Alternatively, in another example, when the cap 350a is in the locked position, the narrow portion 376 of the piston portion 353a may fully extend into the cylindrical recess 381 of the second washer 363a, and the step surface 377 may be in contact with the proximal end of the second washer.

FIGS. 4A-4D show a locking hub 430 that is a variant of the locking hub 330 and also suitable for use with the delivery device 100 of FIGS. 1A and 1B in place of the hemostasis valve 130. The locking hub 430 has a housing 440 having a lumen including a proximal recess 441 contiguous with a distal socket 442 configured to fixedly receive the proximal end of the outer shaft 126, and configured to slidably receive a portion of the inner shaft 122 extending within the outer shaft. The inner shaft 122 extends from the distal socket 442 through the proximal recess 441 along a longitudinal axis L1. The housing 440 has a flushing port 443 that is in fluid communication with the flush port assembly 134. The locking hub 430 may have a pair of wings 444 extending outwardly from the housing 440 along an axis L2 transverse to the longitudinal axis. The wings 444 may be configured to be grasped by a user of the locking hub 430.

Figure 4A:
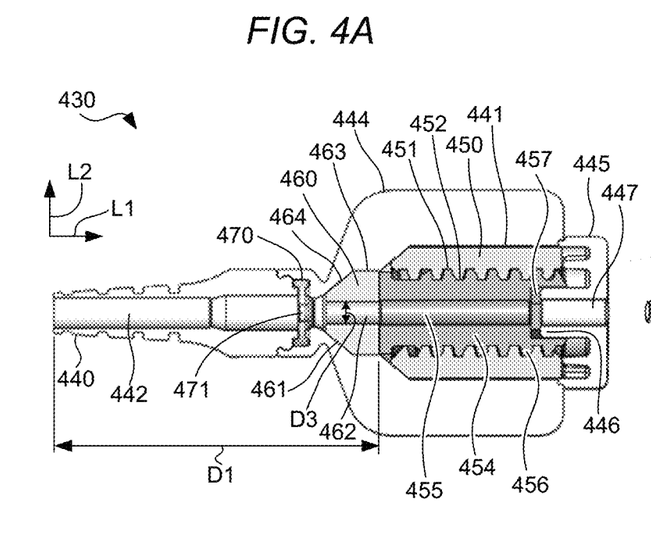
FIG. 4A is a longitudinal cross-section through a locking hub suitable for use with the delivery device of FIGS. 1A and 1B, according to another embodiment, shown in an unlocked position.
Figure 4B:
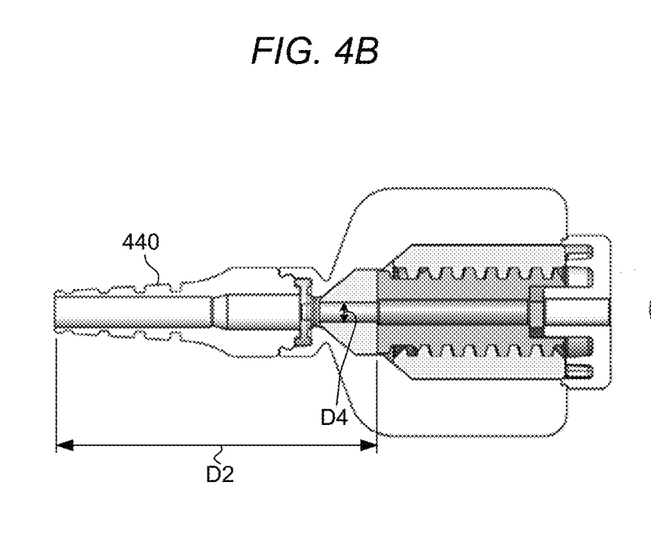
FIG. 4B is a longitudinal cross-section through the locking hub of FIG. 4A, shown in a locked position.

The locking hub 430 may have a retention cap 445 fixedly and securely attached to the housing 440 (using, e.g., one or more adhesives, fasteners, ultrasonic welding, or the like) at the proximal end of the proximal recess 441. The retention cap 445 may have a central alignment portion 446 extending along the longitudinal axis L1. The alignment portion 446 may have any non-circular cross-sectional shape, such as a square, a rectangle, an oval, an X, or the like. The retention cap 445 may have a lumen 447 extending through the alignment portion 446 along the longitudinal axis L1.

Figure 4C:
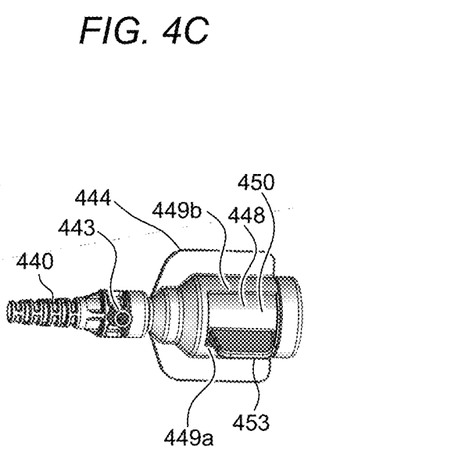
FIG. 4C is a perspective view of the locking hub of FIG. 4A.
Figure 4D:
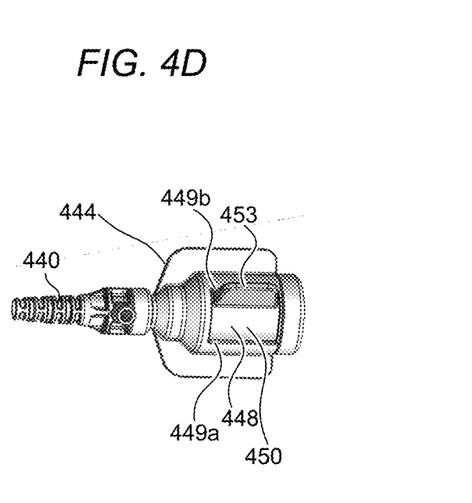
FIG. 4D is a perspective view of the locking hub of FIG. 4B.

The outer circumference of the housing 440 may include a window 448 in communication with the proximal recess 441. The window 448 may have first and second ends 449a and 449b located at predefined circumferential locations about the longitudinal axis L1. The first and second ends 449a and 449b may be separated by a predetermined angular distance. As shown in FIGS. 4C and 4D, the first and second ends 449a and 449b are separated by approximately 90°, but may be separated by other angular distances, such as 30°, 45°, 60°, 120°, 180°, 270°, or other angles in between, among others.

The locking hub 430 may contain a driver 450 rotatably mounted within the proximal recess 441 of the housing 440. The driver 450 is configured to be rotated about the longitudinal axis L1 between the unlocked position shown in FIG. 4A and the locked position shown in FIG. 4B. When the driver 450 is in the locked position, the relative longitudinal locations of the inner shaft 122 and the outer shaft 126 are fixed to one another, as will be explained in more detail below. When the driver 450 is in the unlocked position, the outer shaft 126 and the locking hub 330 are translatable together along the inner shaft 122 in directions of the longitudinal axis L1. The driver 450 may have a central bore

451 extending therethrough along the longitudinal axis L1. The central bore 451 may include a series of internal threads 452 along its length.

A lever 453 may extend radially outwardly from an outer surface of the driver 450 and through the window 448. The lever 453 may be configured to be grasped by a user of the locking hub 430 so that the user can rotate the driver 450 about the longitudinal axis L1 relative to the housing 440 to move the driver between the locked and unlocked positions. The lever 453 may be movable within the window 448 between the first and second ends 449a, 449b as the driver rotates about the longitudinal axis L1. The first and second ends 449a, 449b may limit the movement of the lever 453, thereby together defining a range of rotational movement of the driver 450 that is about equal to the extent of the angular separation between the first and second ends of the window 448, e.g., approximately 90°, that is, about one-quarter turn. The location of the lever 453 of the driver 450 between the wings 444 of the housing 440 may permit a user to lock or unlock the locking hub 430 using one-handed operation, for example, by placing a thumb on the lever 453 and two fingers on the surfaces of the wings 444 opposite the lever 453.

The locking hub 430 may have a core 454 at least partially disposed within the central bore 451 of the driver 450. The core 454 may have a lumen 455 extending therethrough along the longitudinal axis L1 and may include external threads 456 configured to mate with the internal threads 452 of the driver 450, such that the driver and the core 454 may be rotatably coupled to one another. The core 454 may have a recess 457 at its proximal end that extends along the longitudinal axis L1. Recess 457 has a cross-sectional shape that at least partially conforms to the cross-sectional shape of the alignment portion 446 of the retention cap 445.

The alignment portion 446 of the retention cap 445, the driver 450, and the core 454 are together configured so that when the driver is rotated about the longitudinal axis L1, the engagement between the threads 452 of the driver and the threads 456 of the core cause the core to translate distally along the longitudinal axis. The core 454 is prevented from rotating along with the driver 450 due to the engagement of the alignment portion 446 of the retention cap 445 in the recess 457 of the core, as will be described below.

The recess 457 may have any non-circular cross-sectional shape, such as a square, a rectangle, an oval, an X, or the like, such that the shape of the recess at least partially conforms to the shape of the alignment portion 446. It is not necessary that the cross-sectional shape of the recess 457 be entirely conformal with the cross-sectional shape of the alignment portion 446 of the retention cap 445, but the cross-sectional shapes of the recess and the alignment portion should be sufficiently conformal that the alignment portion can prevent the core 454 from rotating relative to the housing 440 when the driver 450 is rotated. For example, if the recess 457 has a square cross-section, the alignment portion 446 could have an X cross-section, permitting the corners of the square and the X to be conformal with one another, thereby preventing relative rotation between the recess and the alignment portion.

The core 454 may abut a clamping gasket 460 having a conical distal surface 461 and a lumen 462 extending therethrough along the longitudinal axis L1. The conical distal surface 461 of the clamping gasket 460 may be received within a distal portion 463 of the proximal recess 441 of the housing having a conical portion 464 configured to mate with the conical distal surface of the clamping gasket. The distal portion 463 of the proximal recess 441 may be formed as a contiguous portion of the housing 440 as shown in FIGS. 4A-4D or may be a separate washer-like component similar to the first washer 263 or the second washer 363 described above. A hemostasis gasket 470 may be positioned between the distal socket 442 and the distal portion 463 of the proximal recess 441. The hemostasis gasket 470 may have an opening 471 extending therethrough along the longitudinal axis L1.

The distal socket 442, the central bore 451, the lumens 447, 455, and 462, and the opening 471 are all axially aligned along the longitudinal axis L1, such that the inner shaft 122 can extend therethrough. Regardless of whether the driver 450 is in the locked position or the unlocked position, the hemostasis gasket 470 is configured to create a liquid-tight seal around the inner shaft 122, thereby preventing blood from leaking out of the proximal end of the catheter assembly 120. However, the force applied by the hemostasis gasket 470 against the inner shaft 122 is low enough to permit the locking hub 430 and the outer shaft 126 to slide longitudinally along the inner shaft when the user retracts the outer shaft and the sheath 128 to deploy the IMD 110.

The core 454 is configured to compress the clamping gasket 460 along the longitudinal axis L1 when the driver 450 is moved from the unlocked position shown in FIG. 4A to the locked position in FIG. 4B. When the driver 450 is in the unlocked position shown in FIG. 4A, the distal end of the core 454 is located a first distance D1 from the distal end of the housing 440, and when the driver is in the locked position shown in FIG. 4B, the distal end of the core is located a second distance D2 from the distal end of the housing, the second distance being less than the first distance. Accordingly, when the driver 450 is moved from the unlocked position shown in FIG. 4A to the locked position shown in FIG. 4B, the core 454 is translated distally along the longitudinal axis L1 by a distance equal to the difference between the first distance D1 and the second distance D2.

When the core 454 is translated distally along the longitudinal axis L1, the clamping gasket 460 is compressed along the longitudinal axis. The clamping gasket 460 is made of a compressible material, such as silicone, rubber, or another polymer. When the clamping gasket 460 is compressed along the longitudinal axis, the conical distal surface 461 of the clamping gasket slides distally along the conical portion 464, and the lumen 462 of the clamping gasket radially compresses from a first diameter D3 (FIG. 4A) to a second diameter D4 (FIG. 4B), the second diameter being less than the first diameter. This reduction in diameter of the lumen 462 of the clamping gasket 460 causes the clamping gasket to compress around the outer surface of the inner shaft 122, thereby fixing the longitudinal position of the inner shaft relative to the outer shaft 126. As a result, the longitudinal position of the IMD 110 relative to the sheath 128 is also fixed so that the IMD is not unintentionally unsheathed as the delivery device is advanced through the vasculature of a patient. When the driver 450 is moved from the locked position back to the unlocked position, the core 454 moves proximally along the longitudinal axis L1, relieving the pressure on the clamping gasket 460 so that the lumen 462 of the clamping gasket radially expands from the second diameter D4 back to the first diameter D3. This radial expansion releases the inner shaft 122 so that the locking hub 430 and the outer shaft 126 may again slide longitudinally along the inner shaft, enabling the sheath 128 to be retracted from around the IMD 110.

The locking hub 430 is configured such that the unlocked position, the locked position, and all intermediate positions therebetween are mechanically stable. For example, when the driver 450 is in the unlocked position shown in FIG. 4A, the compression of the clamping gasket 460 is at a minimum. That is, the distance between the distal end of the core 454 and the distal end of the housing 440 is the first distance D1, which is the farthest distance permitted in any position of the driver 450. Therefore, any rotational motion of the driver 450 will begin to compress the clamping gasket 460 or will further compress the clamping gasket, so the clamping gasket will exert a force against the distal end of the core 454 that will increase the friction between the threads 452 and 456, thereby resisting rotation of the driver and preventing the driver from easily rotating as a result of unintentional contact by a user.

When the driver 450 is in the locked position shown in FIG. 4B or in any intermediate position between the locked and unlocked positions, the distance between the distal end of the core 454 and the distal end of the housing 440 is less than the first distance D1, so the clamping gasket 460 will provide a force against the distal end of the core greater than the force provided when the driver is in the unlocked position. This force against the distal end of the core 454 results in friction between the threads 452 and 456, thereby resisting rotation of the driver 450 and preventing the driver from easily rotating as a result of unintentional contact by a user. In any position of the driver 450, when a user desires to move the driver from the locked position to the unlocked position or vice versa, the user must apply sufficient rotating force to the driver to overcome the friction between the threads 452 and 456.

Although the embodiments herein have been described with the clamping gaskets 260, 360, and 460 being moved and compressed by a movable piston 256, a piston portion 353, or a core 454 against a stationary conical recess 264, 364, or a conical portion 464, that need not always be the case. In a variation, the movable and stationary components may be reversed, such that the clamping gaskets 260, 360, and 460 are stationary, and the conical recess 264, 364, or the conical portion 464 may serve as a movable piston that compresses the respective clamping gasket.

Although the embodiments herein have been described as preventing unwanted relative axial movement between the sheath 128 and the IMD 110 when the catheter assembly 120 bends around curves in the vasculature of a patient, any of the devices and methods described herein may also be incorporated into a delivery device for any other type of medical device that can be delivered into a patient in a compartment that is covered by a distal sheath similar to those described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein describes multiple embodiments of a delivery device for an implantable medical device. The delivery device may include an inner shaft configured to retain the implantable medical device at its distal end, an outer shaft slidably and coaxially disposed about the inner shaft, and a locking hub affixed to the outer shaft. The locking hub may include a housing having an internal recess, a piston element disposed in the internal recess, an actuator operatively coupled to the piston element, and a clamping gasket made of a compressible material and disposed in the internal recess. The piston element may be translatable within the internal recess along a longitudinal axis of the locking hub. The actuator may have a portion thereof extending outside of the housing and accessible for grasping by a user. The actuator may be movable relative to the housing between an unlocked condition and a locked condition. The clamping gasket may have a lumen extending therethrough along the longitudinal axis. The lumen may have a first diameter with the actuator in the unlocked condition and a second diameter with the actuator in the locked condition, the second diameter being less than the first diameter. The outer shaft and the locking hub may be slidable along the inner shaft with the actuator in the unlocked condition. The outer shaft and the locking hub may be fixed to the inner shaft with the actuator in the locked condition; and/or the delivery device may also include a hemostasis gasket separate from the clamping gasket and disposed in the internal recess, the hemostasis gasket being slidably disposed around the inner shaft and providing a liquid-tight seal against the inner shaft, the liquid-tight seal being maintained with the actuator in the unlocked condition and with the actuator in the locked condition; and/or the clamping gasket may have a conical distal surface and a conical recess may be disposed within the internal recess of the housing, the conical recess being configured to mate with the conical distal surface of the clamping gasket; and/or the inner shaft may extend through a lumen of the piston element; and/or the actuator may be rotatable relative to the housing between the unlocked condition and the locked condition; and/or rotation of the actuator may be transformed into linear translation of the piston element along the longitudinal axis of the locking hub; and/or the actuator may be a lever cam rotatable about an axis transverse to the longitudinal axis, the lever cam having a first abutment surface located a first distance from the transverse axis and a second abutment surface located a second distance from the transverse axis, the second distance being greater than the first distance; and/or the first abutment surface may contact the piston element with the actuator in the unlocked condition, and the second abutment surface may contact the piston element with the actuator in the locked condition; and/or the actuator may be a cap that is threadedly engaged with the housing and the piston element may be a portion of the cap, the piston element having an end located a first distance from a distal end of the housing with the cap in the unlocked condition and located a second distance from the distal end of the housing with the cap in the locked condition, the second distance being less than the first distance; and/or the housing may include two protrusions separated by an angular distance and the rotational freedom of the cap may be limited to a predetermined angle of rotation determined by the angular distance; and/or the actuator may be a lever extending from a driver positioned within the internal recess of the housing and the piston element may be threadedly engaged with the driver, the piston element having an end located a first distance from a distal end of the housing with the lever in the unlocked condition and located a second distance from the distal end of the housing with the lever in the locked condition, the second distance being less than the first distance; and/or the housing may include a window having a first end and a second end separated by an angular distance, the lever may protrude through the window, and the rotational freedom of the lever may be limited to a predetermined angle of rotation determined by the angular distance; and/or the housing may include an alignment portion at least partially extending into an alignment recess of the piston element, the alignment portion and the alignment recess together being configured to prevent rotation of the piston element with rotation of the lever between the unlocked condition and the locked condition.

Also described herein are multiple embodiments of a method of delivering an implantable medical device to a target location. The method may include providing a delivery device having an inner shaft configured to releasably retain the implantable medical device at a distal end of the delivery device, an outer shaft slidably and coaxially disposed about the inner shaft, the outer shaft affixed to a sheath that is configured to selectively cover the implantable medical device, and a locking hub having a housing affixed to the outer shaft and an actuator movable relative to the housing between an unlocked condition and locked condition, the locking hub having a hemostasis gasket slidably disposed around the inner shaft.

The method may also include placing the actuator in the locked condition, so that the outer shaft and the locking hub are releasably fixed to the inner shaft, and inserting the distal end of the delivery device into vasculature of a patient. The method may also include advancing the distal end of the delivery device to the target location, moving the actuator to the unlocked condition, so that the outer shaft and the locking hub are slidable along the inner shaft, and sliding the sheath relative to the inner shaft to uncover the implantable medical device. The method may also include releasing the implantable medical device from the inner shaft and removing the distal end of the delivery device from the vasculature of the patient. The hemostasis gasket may provide a liquid-tight seal against the inner shaft, the liquid-tight seal being maintained when the actuator is in the unlocked condition and when the actuator is in the locked condition; and/or the step of moving the actuator to the unlocked condition may include rotating the actuator relative to the housing; and/or the delivery device may include a piston element disposed in an internal recess of the locking hub, wherein the step of rotating the actuator to the unlocked condition includes translating the piston element relative to the housing; and/or the delivery device may include a clamping gasket separate from the hemostasis gasket, the clamping gasket made of a compressible material and disposed in an internal recess of the locking hub, the inner shaft extending through a lumen of the clamping gasket, the lumen having a first diameter with the actuator in the unlocked condition and a second diameter with the actuator in the locked condition, the second diameter being less than the first diameter; and/or the clamping gasket may have a conical distal surface and a conical recess may be disposed within the internal recess of the locking hub, the conical recess configured to mate with the conical distal surface of the clamping gasket; and/or the actuator may be a lever cam rotatable about an axis transverse to the longitudinal axis, the lever cam having a first abutment surface located a first distance from the transverse axis and a second abutment surface located a second distance from the transverse axis, the second distance being greater than the first distance; and/or the actuator may be a cap that is threadedly engaged with the housing and the piston element may be a portion of the cap, the piston element having an end located a first distance from a distal end of the housing with the cap in the unlocked condition and located a second distance from the distal end of the housing with the cap in the locked condition, the second distance being less than the first distance; and/or the actuator may be a lever extending from a driver positioned within the internal recess of the housing and the piston element is threadedly engaged with the driver, the piston element having an end located a first distance from a distal end of the housing with the lever in the unlocked condition and located a second distance from the distal end of the housing with the lever in the locked condition, the second distance being less than the first distance.

The invention claimed is:

1. A delivery device for an implantable medical device, the delivery device comprising:
   an inner shaft configured to retain, at its distal end, a proximal end of the implantable medical device;
   an outer shaft slidably and coaxially disposed about the inner shaft;
   a sheath affixed to a distal end of the outer shaft, the sheath having a compartment configured to receive the implantable medical device such that the sheath selectively covers an anchor at a distal end of the implantable medical device based on sliding the sheath and the outer shaft relative to the inner shaft; and
   a locking hub affixed to a proximal end of the outer shaft, the locking hub including:
      a housing having an internal recess;
      a piston element disposed in the internal recess, the piston element being translatable within the internal recess along a longitudinal axis of the locking hub;
      an actuator operatively coupled to the piston element, the actuator having a portion thereof extending outside of the housing and accessible for grasping by a user, the actuator having first and second abutment surfaces and being movable relative to the housing between an unlocked condition and a locked condition;
      a movement restrictor having fixed surfaces defining limits of movement of the actuator between the unlocked condition and the locked condition, the first abutment surface of the actuator contacting one of the fixed surfaces in the locked condition and the second abutment surface of the actuator contacting another one of the fixed surfaces in the unlocked condition, at least one of the fixed surfaces being formed by an exterior surface of the housing; and
      a clamping gasket made of a compressible material and disposed in the internal recess, the clamping gasket having a lumen extending therethrough along the longitudinal axis, the lumen having a first diameter with the actuator in the unlocked condition and a second diameter with the actuator in the locked condition, the second diameter being less than the first diameter, wherein the outer shaft and the locking hub are slidable along the inner shaft to expose the implantable medical device by retracting the sheath when the actuator is in the unlocked condition, and the outer shaft and the locking hub are fixed to the inner shaft to prevent exposure of the anchor of the implantable medical device when the delivery device is advanced through vasculature of a patient with the actuator in the locked condition.

2. The delivery device of claim 1, further comprising a hemostasis gasket separate from the clamping gasket and disposed in the internal recess, the hemostasis gasket being slidably disposed around the inner shaft and providing a liquid-tight seal against the inner shaft, the liquid-tight seal being maintained with the actuator in the unlocked condition and with the actuator in the locked condition.

3. The delivery device of claim 1, wherein the clamping gasket has a conical distal surface and a conical recess is disposed within the internal recess of the housing, the conical recess being configured to mate with the conical distal surface of the clamping gasket.

4. The delivery device of claim 1, wherein the inner shaft extends through a lumen of the piston element.

5. The delivery device of claim 1, wherein the actuator is rotatable relative to the housing between the unlocked condition and the locked condition.

6. The delivery device of claim 5, wherein rotation of the actuator is transformed into linear translation of the piston element along the longitudinal axis of the locking hub.

7. The delivery device of claim 1, wherein the actuator is a cap that is threadedly engaged with the housing and the piston element is a portion of the cap, the piston element having an end located a first distance from a distal end of the housing with the cap in the unlocked condition and located a second distance from the distal end of the housing with the cap in the locked condition, the second distance being less than the first distance.

8. The delivery device of claim 7, wherein the housing includes two protrusions separated by an angular distance and the rotational freedom of the cap is limited to a predetermined angle of rotation determined by the angular distance.

9. The delivery device of claim 1, wherein the actuator is a lever extending from a driver positioned within the internal recess of the housing and the piston element is threadedly engaged with the driver, the piston element having an end located a first distance from a distal end of the housing with the lever in the unlocked condition and located a second distance from the distal end of the housing with the lever in the locked condition, the second distance being less than the first distance.

10. The delivery device of claim 9, wherein the housing includes a window having a first end and a second end separated by an angular distance, the lever protrudes through the window, and the rotational freedom of the lever is limited to a predetermined angle of rotation determined by the angular distance.

11. The delivery device of claim 9, wherein the housing includes an alignment portion at least partially extending into an alignment recess of the piston element, the alignment portion and the alignment recess together being configured to prevent rotation of the piston element with rotation of the lever between the unlocked condition and the locked condition.

12. The delivery device of claim 1, wherein the locking hub further includes a flushing port attached to the housing and adapted to be connected to a flush port assembly for flushing the compartment in the sheath.

13. The delivery device of claim 1, wherein the first and second abutment surfaces of the actuator are surfaces of a pin.

\* \* \* \* \*